(12) United States Patent
Fitz

(10) Patent No.: US 6,687,911 B2
(45) Date of Patent: Feb. 10, 2004

(54) HANDLING AID FOR A TAMPON FOR FEMININE HYGIENE

(76) Inventor: Martina Fitz, Byinkstrabe 12a, Ascheberg (DE), 59387

( * ) Notice: Subject to any disclaimer, the term of this patent is extended or adjusted under 35 U.S.C. 154(b) by 0 days.

(21) Appl. No.: 09/742,901

(22) Filed: Dec. 21, 2000

(65) Prior Publication Data
US 2001/0049838 A1 Dec. 13, 2001

(51) Int. Cl.$^7$ ............................................. A41D 19/00
(52) U.S. Cl. ..................................... 2/21; 2/163; 2/168
(58) Field of Search ............................. 2/21, 907, 164, 2/158, 159, 160, 16, 20, 161.6, 161.7, 161.8, 163, 168; 206/438, 440, 282; 604/358, 393, 904; 15/227; 294/25

(56) References Cited

U.S. PATENT DOCUMENTS

| | | | | |
|---|---|---|---|---|
| 474,929 A | * | 5/1892 | Tabor et al. | |
| 1,113,870 A | * | 10/1914 | Billings | 2/158 |
| 1,346,683 A | * | 7/1920 | Reynolds | |
| 2,643,388 A | * | 6/1953 | Curtis | 2/158 |
| 2,713,548 A | * | 7/1955 | Whilte et al. | 117/94 |
| 2,773,264 A | * | 12/1956 | Nover | 2/159 |
| 4,645,251 A | * | 2/1987 | Jacobs | 294/1.3 |
| 4,648,867 A | * | 3/1987 | Conner et al. | 604/14 |
| 4,677,697 A | * | 7/1987 | Hayes | 2/159 |
| 4,704,743 A | * | 11/1987 | Thornell et al. | 2/159 |
| 4,751,747 A | * | 6/1988 | Banks et al. | 2/21 |
| 4,902,283 A | * | 2/1990 | Rojko et al. | 604/290 |
| 5,020,160 A | * | 6/1991 | Cano | 2/159 |
| 5,025,503 A | * | 6/1991 | O'Brien | 2/163 |
| 5,169,251 A | * | 12/1992 | Davis | 401/7 |
| 5,542,125 A | * | 8/1996 | Zuckerwar | 2/158 |
| 5,740,554 A | | 4/1998 | Reed | |
| 5,749,097 A | * | 5/1998 | Garrett-Roe | 2/21 |
| 5,766,248 A | * | 6/1998 | Donovan | 623/11 |
| 5,988,386 A | * | 11/1999 | Morrow | 206/581 |
| 6,112,331 A | * | 9/2000 | Horn | 2/163 |
| 6,145,128 A | * | 11/2000 | Suzuki | 2/21 |
| 6,338,163 B1 | * | 1/2002 | Markson | 2/163 |
| D462,485 S | * | 9/2002 | Fowler | D29/113 |
| 6,481,766 B1 | * | 11/2002 | May et al. | 294/1.3 |
| 6,516,469 B1 | * | 2/2003 | Schaetzel | 2/16 |

FOREIGN PATENT DOCUMENTS

| | | |
|---|---|---|
| DE | 2710540 C2 | 9/1977 |
| DE | 2742324 C2 | 3/1978 |
| DE | 3106943 A1 | 9/1982 |
| DE | 3923289 C2 | 10/1990 |
| EP | 0543657 B1 | 5/1993 |
| EP | 0592175 B1 | 4/1994 |

OTHER PUBLICATIONS

U.S. patent application Ser. No. 09/739,046, J&J, filed 1798.

* cited by examiner

Primary Examiner—John J. Calvert
Assistant Examiner—Alissa L. Hoey

(57) ABSTRACT

Handling aid for a tampon for feminine hygiene having at least two separate finger coverings for the user. At least one finger covering of the handling aid is joined to the finger covering by a line of weakness in such a way that it is at least partially detachable from the remaining part of the handling aid. The handling aid can be produced from two essentially planar portions of film corresponding to the outline of the handling aid, the outline of the aid being thermally or mechanically joined with an edge unjoined to provide a reaching-in opening. The handling aid can also be produced by dipping.

34 Claims, 6 Drawing Sheets

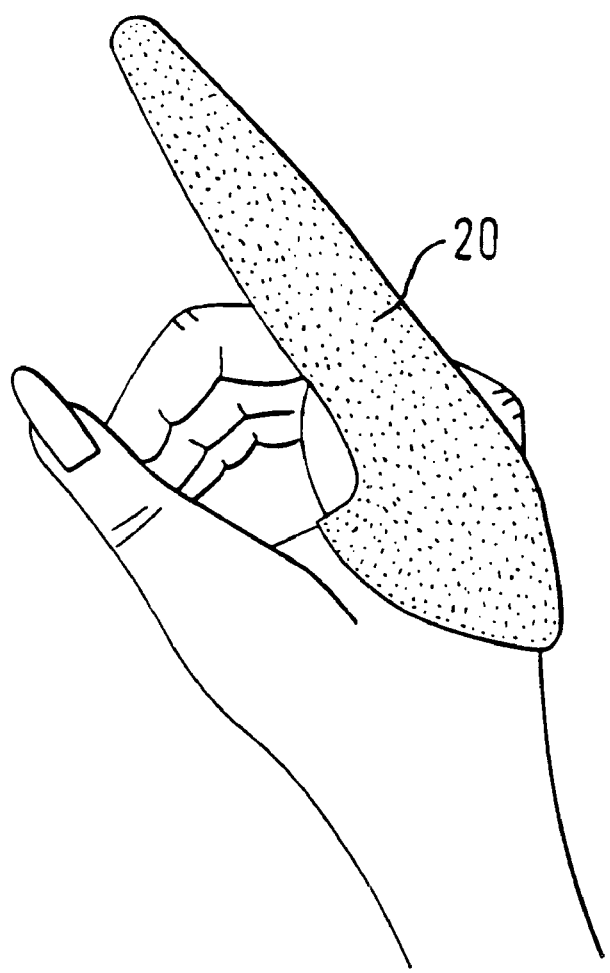

HANDLING AID FOR A TAMPON FOR FEMININE HYGIENE

CROSS-REFERENCE TO RELATED APPLICATIONS

This invention is related to German Patent Application No. 199 63 518.8, filed Dec. 28, 1999, and U.S. Ser. No. 09/739,046, filed Dec. 18, 2000, entitled "Handling aid for a tampon for feminine hygiene", the disclosures of which are herein incorporated by reference.

FIELD OF THE INVENTION

The invention relates to a handling aid for a tampon for feminine hygiene, having at least two separate finger coverings for a user, one of which is removable from the handling aid.

BACKGROUND OF THE INVENTION

A handling aid for tampons is disclosed in U.S. Pat. No. 5,740,554. In this document there is disclosed a protective glove for the hygienic removal of a tampon from the body cavity of a user and for subsequent disposal of the used tampon. The glove comprises a separate finger covering for the thumb and a partially separate finger covering for the index finger. A single covering, similar to a mitten covers the other areas of the fingers and hand.

Following removal of the tampon from the body cavity, it is wrapped up by turning the glove inside out, so that the tampon is essentially completely enclosed. Thus, only the inner surface of the glove, which has not contacted the used tampon, now lies on the outside. This permits hygienic disposal of the soiled tampon.

In particular when traveling or if the accustomed hygiene conditions are not encountered, however, not only hygienic disposal of a tampon is a problem for the user, but also the hygienic insertion of a new tampon into the body cavity.

SUMMARY OF THE INVENTION

It is accordingly an object of the present invention to provide a handling aid for a tampon, for feminine hygiene with which both hygienic disposal of the used tampon and hygienic insertion of a new tampon into the body cavity are ensured in as simple and inexpensive a way as possible, even in the case of inadequate sanitary installations or poor hygiene conditions.

The present invention relates to a handling aid suitable for use with a tampon for feminine hygiene. The aid has at least two separate finger coverings for a user. At least one of these individual finger coverings is joined to the remainder of the handling aid by a line of weakness in such a way that the said finger covering is at least partially detachable from a remaining part of the handling aid.

A method of producing the handling aid can include the steps of dipping a former into a liquid, film-forming material to form a handling aid and forming a line of weakness in the handling aid. The former has at least two separate lobes corresponding to finger coverings to form a handling aid having at least two separate finger coverings for a user. Further, one of the finger coverings is at least partially detachable from a remaining part of the handling aid.

Another method of producing the handling aid includes the steps of thermally bonding together a first essentially planar film and a second essentially planar film in a pattern corresponding to an outline of the shape of the handling aid, and protecting an edge region of the films from thermal bonding to form an opening in the handling aid.

BRIEF DESCRIPTION OF THE DRAWINGS

These and further advantages and features of the invention are described in more detail below with reference to the attached schematic drawings, in which:

FIGS. 2a to 2e show individual steps in the use of a handling aid shown in FIG. 1.

DESCRIPTION OF THE PREFERRED EMBODIMENTS

Figure 1:
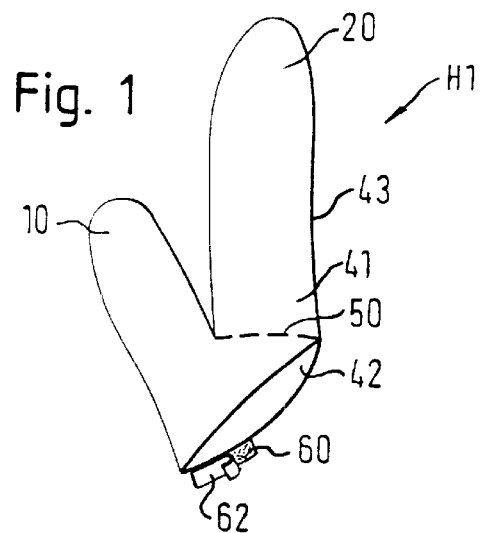
FIG. 1 shows a first embodiment of the handling aid.

According to the invention, the at least two protective finger coverings are formed such that they can be detached essentially completely from one another. The user can therefore use the handling aid to remove a tampon hygienically from the body cavity, then detach at least one of the finger coverings from the rest of the handling aid and wrap the used tampon up in the detached finger covering in order to dispose of said tampon hygienically. For example, turning the finger covering inside out can do this. With the aid of the least one remaining finger covering, the user can insert a new tampon hygienically into the body cavity, without having to touch the new tampon or regions of the body cavity directly with her possibly soiled hands or fingers.

The handling aid preferably has a line of weakness between two finger coverings, in order to establish a separating line for the region of the handling aid that is used for the disposal of the used tampon. As a result, the separation of the finger coverings can be carried out in a defined manner and always at the same place, so that, on the one hand a specific region is detachable for completely covering and enclosing the used tampon. In addition, an adequate part of the handling aid remains to be used to hygienically insert a new tampon. Unwanted tearing of the material, which could impair the function of the handling aid, is avoided.

The line of weakness may be a continuous line of weakness, so that the part of the handling aid to be detached for disposal can be completely detached and disposed of directly. It is also possible, however, to provide a line of weakness that is not completely continuous. Thus, although wrapping up of the used tampon is possible after destroying the line of weakness, the wrapped-up tampon continues to be in connection with the part of the handling aid envisaged for the insertion of a new tampon. Therefore, after insertion of the new tampon it is possible to dispose of the handling aid with the used tampon as a whole. Functional impairments do not occur as a result. The used tampon is completely shielded from the outside, for example by turning a detached finger covering inside out, so that the used tampon does not cause undesired soiling.

The line of weakness is preferably a line with a reduced material thickness. As a result, On the one hand adequate stability of the handling aid is ensured, which prevents inadvertent destruction of the line of weakness, on other hand intentional, defined destruction of the line of weakness is permitted. In addition, there are no openings in the material, so that the most stringent hygiene requirements are satisfied and complete shielding of the fingers of the, user is ensured.

In the case of another embodiment, a perforated line defines the line of weakness. Such a perforated line is simpler in terms of technical production aspects and consequently less costly than the line of weakness with reduced material thickness described above. In this embodiment, the perforation holes may be very small, so that even in this case stringent hygiene requirements are satisfied and fluid cannot generally penetrate through the perforation holes. Protection against fluid penetrating through the perforation holes may also be additionally achieved, if appropriate, by a water-repellent coating, for example a lacquer, or by corresponding material of the glove.

For the geometrical design of the handling aid, there are many possibilities. The handling aid preferably comprises a finger covering for the thumb and a finger covering for the index finger. As a result, the tampon can be hygienically removed from the body cavity. In this embodiment, the used tampon is wrapped up in the finger covering for the thumb, which is detachable from the finger covering for the index finger. A new tampon is then inserted with the finger covering for the index finger. The desired objectives can therefore be realized with least expenditure on material.

It is also possible to provide at least two finger coverings for not directly neighboring fingers, for example for the thumb and the middle finger. The finger coverings may also be geometrically designed such that the user is largely free to choose the fingers to be used. In this way, maximum, individual convenience can be achieved.

In a further embodiment, a third finger covering is provided for the middle finger. As a result, the user can remove the tampon from the body cavity with two fingers, then dispose of it and hygienically insert the new tampon with the third finger covering, which has not touched the used tampon. In this embodiment, the line of weakness may be provided between the finger covering for the thumb and the two other finger coverings, so that the disposal is carried out as in the case of the exemplary embodiment described above. Although this is preferred, it is also possible to provide the line of weakness between the finger coverings for the thumb and the index finger on the one hand and the finger covering for the middle finger on the other hand.

It goes without saying that other embodiments are conceivable. In particular, an embodiment with two finger coverings, one for the thumb and another for the index finger and middle finger is envisioned. Alternatively, a handling aid with three finger coverings, one finger covering being provided for the thumb and one finger covering being provided for the index finger and middle finger and one for the ring finger and little finger is possible.

Furthermore, it is possible to use a handling aid in the form of a mitten, in which one finger covering is provided for the thumb and one finger covering is provided for the remaining fingers. In the case of such a form of mitten, it is advantageous that, along with the thumb region, a further finger is of a partially separate design, in order to facilitate insertion of the new tampon. Such a partially separate design may in this case extend over for instance one to two phalanxes.

Depending on the embodiment, only said fingers are covered by the finger coverings, but it is also possible, by a correspondingly enlarged handling aid, for parts of the palm of the hand or the back of the hand to be covered.

It is possible to provide handling aids both for the left hand and for the right hand and to form them relatively exactly, if appropriate in various sizes. It is preferred, however, to provide symmetrical handling aids, in particular in a standard size, which can be used both for the left hand and for the right hand.

In an advantageous embodiment, the part of the handling aid that is envisaged for the disposal of the tampon is provided with a closure. As a result, the disposed-of tampon can, after wrapping up, for example by turning a finger covering inside out, be securely closed in its wrapping, so that hygienic disposal is possible, even with other customary garbage, and an escape of fluid is reliably prevented. An adhesive closure, in particular a pressure-sensitive adhesive closure, may be provided as the closure. The part of the adhesive closure that is covered with an adhesive is in this case preferably provided with a pull-off covering, which is pulled off before sealing the wrapping with the tampon enclosed. However, it is also possible to insert into the covering material a thread with which the part of the handling aid envisaged for disposal can be closed off.

Different adhesives, both adhesion adhesives and cohesion adhesives, may be used for the adhesive closure. The adhesives that can be used can be subdivided into physically setting adhesives and chemically setting adhesives.

The physically setting adhesives include hot-melt adhesives, such as SB (styrene-butadiene copolymers), EVA (ethylene-vinyl-acetate), polyesters; plastisol adhesives, such as for example PVC+plasticizer+coupling agent; pressure-sensitive adhesives, such as rubbers or polyacrylates; contact adhesives, such as PUR (polyurethane plastics) SB (styrene-butadiene copolymers); solvent/dispersion adhesives, such as VA (vinyl-acetate), VC (vinylchloride), VDC (vinylidene chloride) copolymers, EVA (ethylene-vinyl-acetate) or polyacrylates; or else glues based on starch, dextrin, PVAL (polyvinyl alcohol) or cellulose ether.

The chemically setting adhesives include, for example, reaction adhesives, such as for example EP (epoxy)+anhydrides, EP (epoxy)+polyamines, polyisocyanates+polyols, cyanoacrylates or UP (urethane polyester resins)+styrene or methacrylate.

In a preferred embodiment of the handling aid for the tampon, a new tampon can be hygienically packed in it and protected against contamination and moisture, so that there is no need for additional packaging and packaging material is saved.

The new tampon may be packed, for example, in one of the finger coverings, it also being possible here to provide a releasable sealing or an easy-to-open closure, in order that the new tampon is hygienically packed in the closed-off finger covering until it is used.

In a further embodiment of the handling aid according to the invention, an absorbent material is provided on the outer side, preferably at a region of the handling aid that is used for the disposal of the used tampon. The tampon removed from the body cavity is placed onto this absorbent material, so that possibly escaping fluid can be absorbed and soiling by fluid can be avoided.

In a further advantageous embodiment, both the tip of the thumb and a second finger tip of the second finger covering are provided with an absorbent material. As a result, the used tampon is easier to handle. Furthermore, all the regions of the handling aid that can come into contact with the used tampon have an absorbent material, in order to absorb fluid immediately and reliably and to avoid soiling.

Different absorbent materials may be used, in particular nonwoven materials, fibrous materials and foam-based materials. Furthermore, the absorbent material may contain superabsorbents, which can absorb many times their own weight of fluid.

The handling aid preferably comprises a plastic film, because this material is generally both impermeable to fluid and very inexpensive and at the same time has small packing dimensions and adequate stability, in order to avoid unwanted tearing of the handling aid.

For reasons of environmental protection, a degradable material is preferably used for the handling aid. Biodegradable materials with different degrading speeds may be used. A minimum degrading time is around 5 minutes, in order that the user has adequate time to wrap the used tampon in part of the handling aid and dispose of it before the degradable material noticeably breaks up.

Particularly preferred is a degrading time of one week to one month, whereby it is generally ensured that the tampon is disposed of in its state of being enclosed by the handling aid in a sealed manner by a disposal company within the regular time period. Suitable in particular as degradable materials are materials which have at least one polyester, in particular from the family of poly-α-hydroxyl acids, such as polytrimethylene carbonate, polydioxanone, poly-glycolide, polyactide, poly-(L-lactide-coglycolide) along with their copolymers with one another, polyorthoester and/or polycaprolactone, polyhydroxybutyrate or polyhydroxybutyrate-co-hydroxyvalerate. The polyhydroxybutyrate-co-hydroxyvalerate preferably has a valerate content of between 5 and 25%.

The degrading rate or degrading speed of the individual materials can be controlled by adding filler materials, for example starch, or by the choice of chain lengths or the number of branches.

In addition to these materials, suitable as further materials are also EVA (ethylene-vinyl-acetate), EMA (ethylene-maleic anhydride copolymers), PP (polypropylene) or PE (polyethylene).

An essentially opaque or colored material is preferably used, so that the disposal of the used tampon can take place discreetly and without being made visible.

The handling aid may be coated on its inner side with a skin-friendly medium and/or with an antiallergenic.

The invention also relates to a method of production for producing the handling aid according to the invention described above. All methods of producing gloves, in particular medical gloves, known in the prior art may be used.

Suitable in particular are dip-molding methods, in which a former which corresponds to the desired shape of the handling aid is dipped once or preferably a number of times into a solution of the desired material.

The material thickness of the handling aid and its characteristic properties, in particular extensibility, tear resistance etc., can be determined by the choice of material and the number of dip-molding operations.

It is also possible by successive dip-molding operations into different solutions to achieve a specific layer structure of the material, with which the characteristic properties can likewise be influenced.

Such methods are known, for example, from DE 27 42 324 C2, EP 0 592 175 B1 or EP 0 543 657 B1.

It is also possible to produce the handling aid from two essentially planar portions of film corresponding to the outlines of the shape of the handling aids. The portions of film are in this case welded or thermally bonded to one another, in their edge regions, so that the desired handling aid is created.

The films may firstly be cut and then joined to one another, but it is preferred for two webs of film to be laid one over the other. The two films are welded at the desired joining line and severed from the film material in the desired shape simultaneously, in a single processing step. The severing of the films may be carried out thermally or mechanically or by both methods combined.

For better handling or as packaging, the film handling aids may be fastened or adhesively attached to a substrate, in particular made of paper, in such a way they can be pulled off. The adhesion of the handling aid an the material of the substrate may be brought about both thermally, in particular in a process taking place simultaneously with the thermal welding of the films of the handling aid, or else means of adhesives.

Preferably only individual regions of the handling aid are fastened to the substrate, but it is also possible to fasten the handling aid to the substrate over its full surface area.

It is also possible to use further known methods of processing films and plastics materials.

The line of weakness is preferably made in the material of the handling aid by processing tools with the application of heat and/or pressure.

The invention also relates to use of the handling aids described above as a disposal aid for a used tampon and as an insertion aid for a new tampon.

FIG. 1 shows a first embodiment of a handling aid H1 having a finger covering 10 for the thumb and a finger covering 20 for the index finger of the user. The two finger coverings 10, 20 can be detached completely from one another by a continuous line of weakness 50, the finger covering 10 envisaged for disposal having an adhesive closure 60 at the lower end. The part of the adhesive closure 60 that is coated with adhesive is provided with a protective covering 62, which is pulled off before the sealing of the finger covering to be detached.

The line of weakness 50 has a reduced thickness in comparison with the other material, so that the handling aid H1 has a completely closed-off surface.

The embodiment of the handling aid H1 represented comprises two essentially planar EVA films 41, 42, which are welded to one another in the region of the edge contours 43 of the fingers or finger coverings. The handling aid H1 can therefore be produced at very low cost.

Figure 2A:
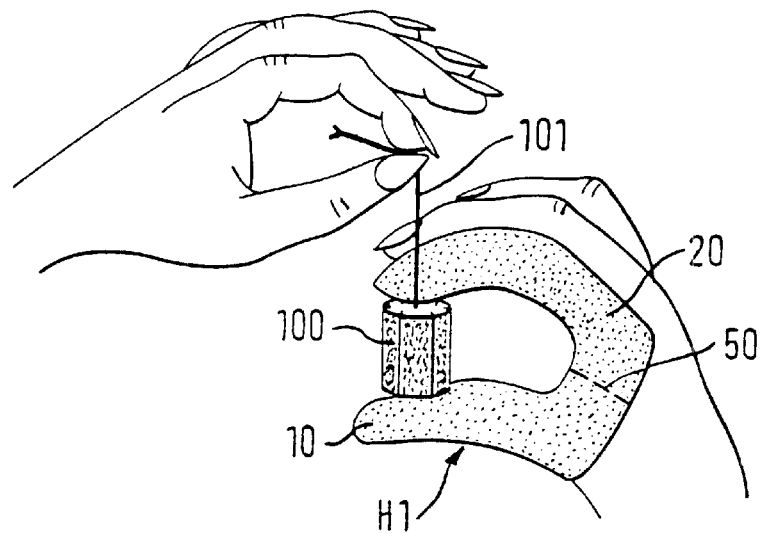
Figure 2B:
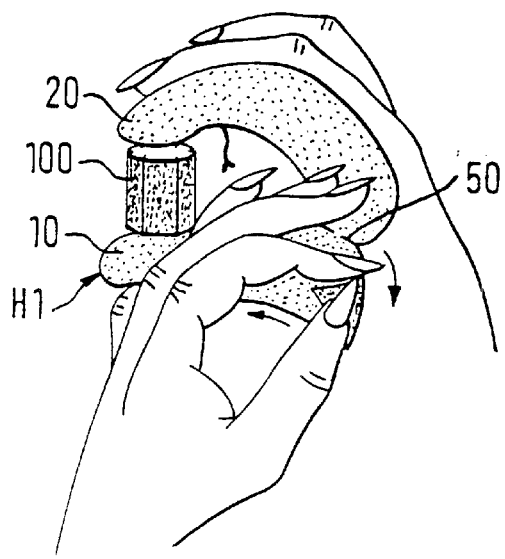
Figure 2C:
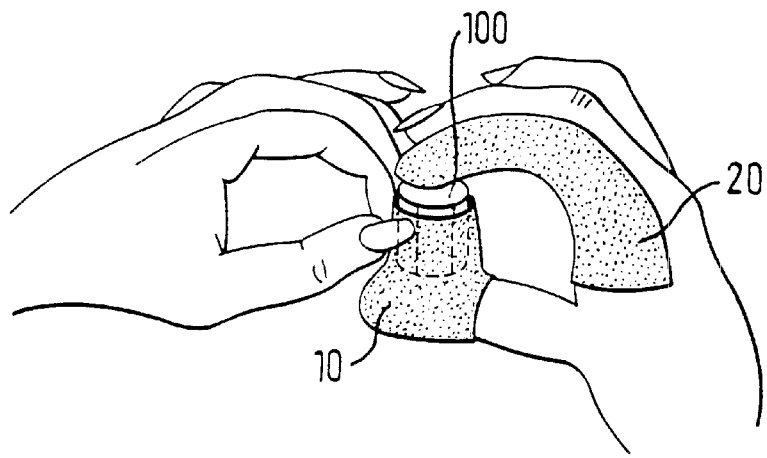
Figure 2D:
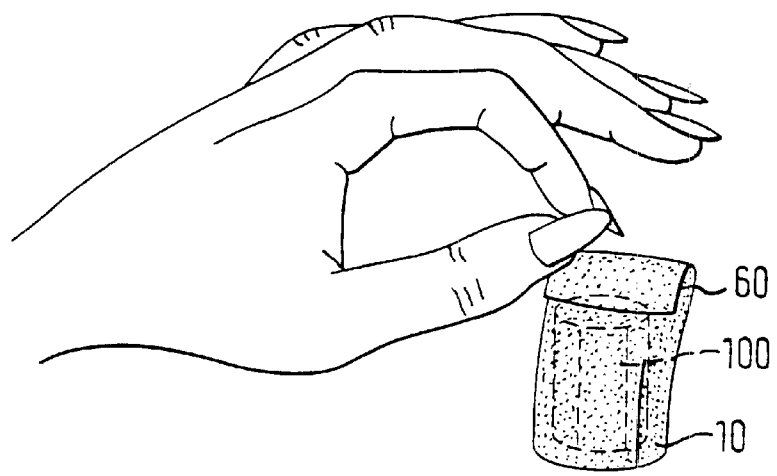

FIGS. 2a to 2e show phases of the use of a handling aid as it is depicted in FIG. 1. According to FIG. 2a, the thumb and the index finger of the right hand of a user are covered by the handling aid H1. A tampon 100 is held by its retrieval string 101 with the left, uncovered hand and is placed between the thumb and index finger of the right hand, the line of weakness 50 with reduced material thickness being provided between the finger coverings 10, 20. The rear part of the finger covering 10 for the thumb is then grasped (FIG. 2b), and is separated along the line of weakness 50 from the finger covering 20 and turned inside out over the thumb of the user in the direction of the arrows toward the tip of the thumb and is drawn over the used tampon 100 (FIG. 2c). The finger covering 10 consequently forms a pocket in which the tampon 100 can be completely closed by means of an adhesive bond 60 and hygienically disposed of (FIG. 2d). With the remaining finger covering 20 for the index finger, the new tampon can then be hygienically inserted into the body cavity (FIG. 2e).

Figure 3:
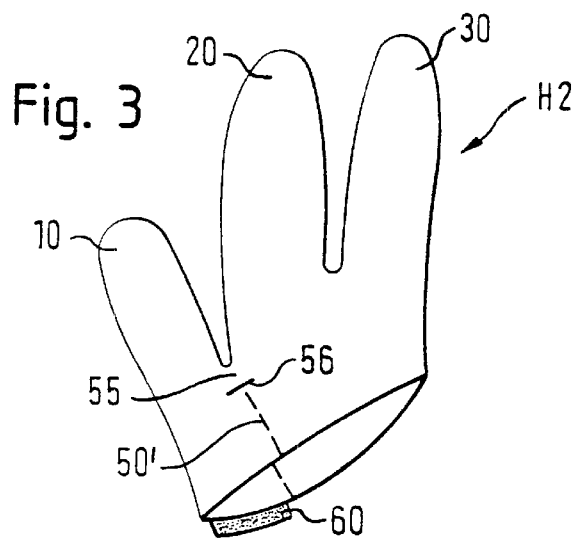
FIG. 3 shows a second embodiment-of a handling aid.

FIG. 3 shows a second embodiment of a handling aid H2. In addition to the finger coverings 10 and 20 for the thumb and index finger, this embodiment comprises a third finger covering 30 for the middle finger. As in the case of the exemplary embodiment explained above, a line of weakness 50' is located between the finger covering 10 for the thumb and the finger covering 20 for the index finger.

As a result, the handling and disposal of the used tampon can be carried out with the thumb and index finger, while the new tampon is inserted into the body cavity with the middle finger covered by the third finger covering 30. Thus, this finger covering 30 remains unsoiled as it does not come into contact with the used tampon.

By contrast with the embodiment shown in FIG. 1, the line of weakness 50' is not continuous, but has an interruption 55 and two reinforcements 56 (only one on the front side is shown), which separate the interruption 55 from the line of weakness 50' in order to avoid unwanted tearing. This makes it possible to enclose and pack the used tampon by turning the finger covering 10 inside out, without the finger covering 10 being completely separated from the remaining handling aid H2, namely the finger coverings 20, 30. Therefore, after insertion of the new tampon into the body cavity, the entire handling aid H2 can be disposed of completely and in one piece. In this embodiment also, an adhesive closure 60 at the lower end of the finger covering 10 serves as the closure. A pressure-sensitive adhesive is applied to the adhesive closure; a protective covering as in the case of the embodiment represented in FIG. 1 may also be provided here.

Figure 4:
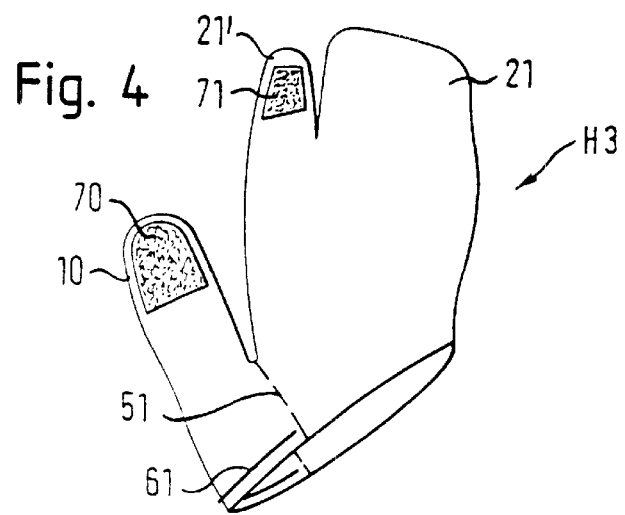
FIG. 4 shows a third embodiment of a handling aid.

FIG. 4 shows a third embodiment of a handling aid H3 in the form of a mitten, having a finger-covering 10 for the thumb and a finger covering 21 for the remaining fingers. The finger covering 21 has a separate region 21', which extends approximately over the length of a phalanx of the index finger, in order to facilitate insertion of a new tampon. The line of weakness 51 is a continuous perforated line that permits complete detachment of the finger covering 10 from the finger covering 21, 21'. In this embodiment, a thread 61 in the lower region is provided as the closure for the finger covering 10 and, by drawing together after wrapping up the tampon, largely shields the latter from the outside.

In addition to the embodiments shown in FIGS. 1 to 3, a layer of an absorbent material 70 is provided on the finger covering 10 for the thumb and a second layer of an absorbent material 71 is provided on the separate region 21, of the finger covering 21. The absorbent material 70, 71 contains superabsorbent material, which can absorb many times its own weight of fluid and does not give off or lose any absorbed fluid, even under pressure.

During removal and disposal, the used tampon only comes into contact with the absorbent material 70, 71 before the turning inside out of a finger covering and the wrapping up, so that possibly escaping fluid is immediately absorbed and soiling is avoided. After removal, the tampon is positioned at least partially on the material 70, so that, even after wrapping up of the tampon and disposal, fluid escaping from the tampon is absorbed.

Figure 5:
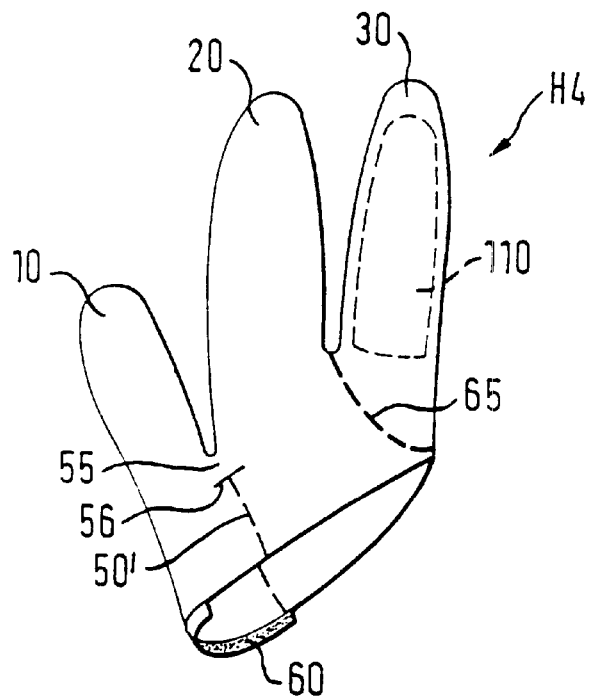
FIG. 5 shows a fourth embodiment of a handling aid.

FIG. 5 shows a fourth embodiment of a handling aid H4 according to the invention, which essentially corresponds to the handling aid H2 shown in FIG. 3. The same elements are provided with identical designations.

In addition to the handling aid H2 shown in FIG. 3, a new tampon 110 is packed in the finger covering 70 of the handling aid H4 shown in FIG. 5. In the case of the embodiment shown in FIG. 5, the tampon merely lies loosely in the finger covering 30. However, it is adequately held in place by the finger covering 30. It may also be envisaged, however, to fasten the tampon 110 releaseably to an inner region of the finger covering 30, for example by an adhering point.

The finger covering 30 of the handling aid H4 is closed off from the outside and with respect to the other finger coverings 10, 20 by a sealing closure 65. This creates in the finger covering 30 a closed-off and hygienically sealed space in which the new tampon 110 can be hygienically stored until use.

The sealing closure 65 may be formed, for example, by adhesives, as have already been described above in connection with the adhesive closure 60. It is also possible, however, to provide a purely mechanical connection between the two sides of the handling aid H4, for example by two opposite linear connecting elements which engage mechanically in one another.

The sealing closure 65 is designed in such a way that it can be easily opened by the user, without damaging the surface of the handling aid H4. It is also possible to provide a recloseable sealing closure 65.

It goes without saying that it is also possible, depending on the geometry of the handling aid H4 provided, for the new tampon 110 to be introduced into other finger coverings 10, 20 for storage.

Figure 6:
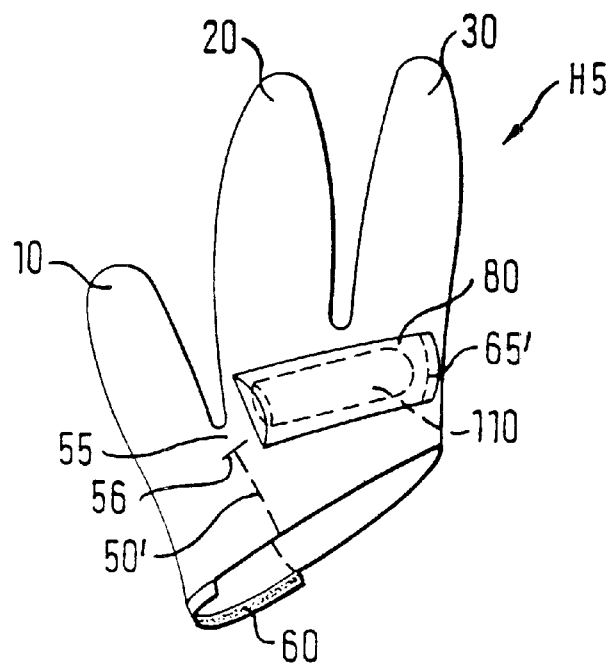
FIG. 6 shows a fifth embodiment of a handling aid.

According to FIG. 6, it is also possible to provide an additional storage pocket 80, for example on an outer region of the handling aid H4 for storing the new tampon 110 instead of the possibility of storage within a finger covering of the handling aid. In this case as well, the storage pocket 80 can be hygienically closed by a sealing closure 65', which comprises the mechanical or adhesive connecting elements already mentioned above. Otherwise, the embodiment represented in FIG. 6 corresponds to the embodiment represented in FIG. 5.

Figure 7:
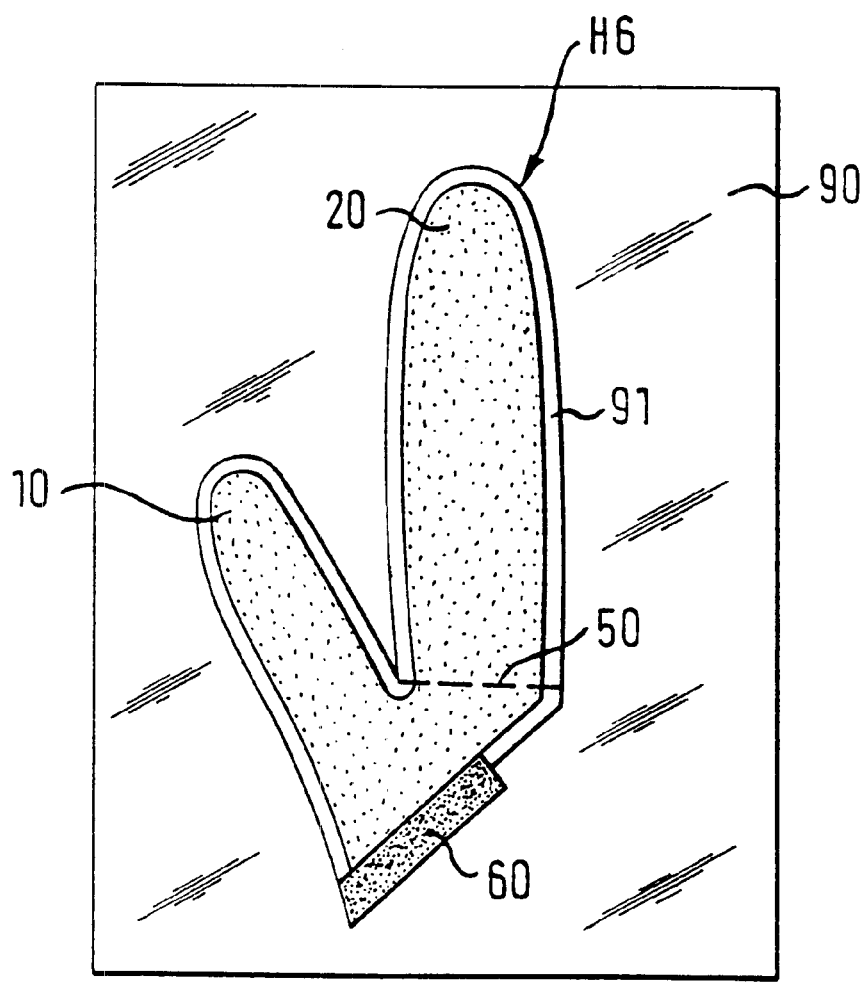
FIG. 7 shows a sixth embodiment of a handling aid, which is fastened to a substrate.

FIG. 7 shows a handling aid H6 that essentially corresponds to the handling aid represented in FIG. 1; therefore, identical or comparable parts have been provided with identical designations.

The handling aid is attached to a paper substrate 90 by means of an adhesive. Preferably, only an edge region 91 of approximately 3 to 5 mm of the handling aid is bonded to the substrate 90. The paper substrate 90 serves as packaging for the handling aid H6, and it is possible for the paper substrate 90 to be both folded and rolled together with the handling aid H6. The paper substrate 90 therefore protects the handling aid H6 against damage before actual use and makes handling easier.

The substrate may also consist of other materials, in particular plastic materials. Furthermore, the handling aid may also be fastened to the substrate by means of other methods and means, for example by slight superficial melting. It is particularly preferred for the substrate to have material which has a lower melting point than the handling aid, or is coated with such a material, in order not to damage the handling aid when it is attached to the substrate.

As already explained in the introductory part of the description, it goes without saying that it is also possible to realize other geometries of the handling aid, without departing from the subject matter of the invention.

The specification and embodiments above are presented to aid in the complete and non-limiting understanding of the invention disclosed herein. Since many variations and embodiments of the invention can be made without departing from its spirit and scope, the invention resides in the claims hereinafter appended.

What is claimed is:

1. A handling aid suitable for use with a tampon for feminine hygiene comprising a film material that is impermeable to fluid and disposable on a user's band wherein a single handling aid forms a fluid impermeable barrier thereon, has at least two separate finger coverings for a user's single hand, a first finger covering joined to a second finger covering across a line of weakness in such a way that the first finger covering is removable from the remaining part of the single handling aid.

2. The handling aid as claimed in claim 1, wherein the line of weakness is disposed between two finger coverings.

3. The handling aid as claimed in claim 2, wherein the line of weakness is continuous and the at least one finger covering of the handling aid can be detached completely from the remaining part of the handling aid.

4. The handling aid as claimed in claim 2, wherein the line of weakness is interrupted at least in a subregion.

5. The handling aid as claimed in claim 1, wherein the line of weakness is a line with reduced material thickness.

6. The handling aid as claimed in claim 1, wherein the line of weakness is a perforated line.

7. The handling aid as claimed in claim 1, wherein the first finger covering is arranged and configured to cover a user's thumb, and the second finger covering is arranged and configured to cover an index finger, and further comprising a third finger covering arranged and configured to cover a middle finger of a user's hand.

8. The handling aid as claimed in claim 1, wherein the first finger covering is arranged and configured to cover a user's thumb and the second finger covering is arranged and configured to cover both an index and a middle finger of a user's hand.

9. The handling aid as claimed in claim 1, wherein the first finger covering is arranged and configured to cover the thumb, and the second finger covering is arranged and configured to cover both an index and a middle finger of a user's hand, and further comprising a third finger covering arranged and configured to cover both a ring and a little finger of a user's hand.

10. The handling aid as claimed in claim 1, wherein the first finger covering is arranged and configured to cover a user's thumb and the second finger covering is arranged and configured to cover the remaining fingers of a user's hand.

11. The handling aid as claimed in claim 1, wherein one of the at least two finger coverings is provided with a closure.

12. The handling aid as claimed in claim 11, wherein the closure is an adhesive closure.

13. The handling aid as claimed in claim 12, wherein the adhesive closure comprises a physically setting adhesive.

14. The handling aid as claimed in claim 12, wherein the adhesive closure comprises a chemically setting adhesive.

15. The handling aid as claimed in claim 11, wherein the closure comprises a thread in the finger covering material.

16. The handling aid as claimed in claim 1, further comprising a tampon packaged in one of the at least two finger coverings.

17. The handling aid as claimed in claim 16, wherein the tampon is contained within the one of the at least two finger coverings by a sealing closure which is capable of being opened by hand for to remove the tampon.

18. The handling aid as claimed in claim 1, which further comprises an absorbent material at least on part of an outer side of the handling aid.

19. The handling aid as claimed in claim 18, wherein a tip region of the first finger covering and a tip region of the second finger covering are provided at least partially with the absorbent material.

20. The handling aid as claimed in claim 1, wherein the at least two finger coverings comprise a plastic film.

21. The handling aid as claimed in claim 20, wherein the plastic film comprises a thermoplastic material which has at least one polyester from the group consisting of poly-α-hydroxyl acids, such as polytrimethylene carbonate, polydioxanone, polyglycolide, polyactide, poly (L-lactide-coglycolide) along with their copolymers with one another, polyorthoester and/or polycaprolactone, polyhydroxybutyrate or polyhydroxybutyrate-co hydroxyvalerate.

22. The handling aid as claimed in claim 21, wherein the thermoplastic material comprises a copolymer of polyhydroxybutyrate-cohydroxyvalerate which has a valerate content of between 5 and 25%.

23. The handling aid as claimed in claim 20, wherein the thermoplastic material comprises EVA (ethylene-vinyl acetate) or EMA (ethylene-maleic anhydride) copolymers or PP (polypropylene) or PE (polyethylene).

24. The handling aid as claimed in one of the preceding claims, wherein it at least partially consists of essentially opaque material.

25. The handling aid as claimed as claimed in claim 1, wherein the at least two finger coverings comprise a biodegradable material.

26. The handling aid as claimed in claim 1, further comprising a substrate on which the at least two finger coverings are removably disposed.

27. The handling aid as claimed in claim 26, wherein the substrate comprises paper.

28. The handling aid as claimed in claim 26, wherein the substrate comprises polymeric material.

29. The handling aid as claimed in claim 28, wherein the polymeric material has a lower melting point than the material of the handling aid.

30. The handling aid as claimed in claim 26, wherein the substrate comprises paper coated with a polymeric material.

31. The handling aid as claimed in claim 30, wherein the polymeric material has a lower melting point than the material of the handling aid.

32. A method of disposing of a tampon comprising the steps of:
   a) removing a soiled tampon;
   b) at least partially detaching one finger covering from a handling aid comprising at least two separate finger coverings for a user, wherein at least one finger covering of the handling aid is joined to the finger covering by a line of weakness in such a way that the said finger covering is at least partially detachable from a remaining part of the handling aid;
   c) enclosing the soiled tampon in the detached finger covering by turning this finger covering inside out, for hygienic disposal; and
   d) disposing of the soiled tampon.

33. The handling aid as claimed in claim 1, wherein the first finger covering is capable of farming a pocket that is removable from the remaining part of the handling aid.

34. The handling aid as claimed in claim 1, wherein the at least one finger covering of the handling aid is integral with the handling aid.

* * * * *